United States Patent
Auerbach et al.

(10) Patent No.: US 9,919,241 B1
(45) Date of Patent: Mar. 20, 2018

(54) EXTRACTION METHOD

(71) Applicant: Entheo Gardens Inc, Portland, OR (US)

(72) Inventors: Michael I Auerbach, Oak Grove, OR (US); William L Reilly, Portland, OR (US)

(73) Assignee: Entheo Gardens Inc, Portland, OR (US)

( * ) Notice: Subject to any disclaimer, the term of this patent is extended or adjusted under 35 U.S.C. 154(b) by 0 days.

(21) Appl. No.: 15/634,933

(22) Filed: Jun. 27, 2017

(51) Int. Cl.
*B01D 11/02* (2006.01)
*C07D 311/80* (2006.01)
*C07C 7/10* (2006.01)
*C07C 7/00* (2006.01)

(52) U.S. Cl.
CPC .......... *B01D 11/0203* (2013.01); *C07C 7/005* (2013.01); *C07C 7/10* (2013.01); *C07D 311/80* (2013.01)

(58) Field of Classification Search
CPC .................................................. B01D 11/0203
USPC .......................................................... 549/390
See application file for complete search history.

(56) References Cited

U.S. PATENT DOCUMENTS

| | | |
|---|---|---|
| 7,344,736 B2 | 3/2008 | Whittle et al. |
| 9,327,210 B1 | 5/2016 | Jones |
| 9,655,937 B2 | 5/2017 | Jones |
| 9,669,328 B2 | 6/2017 | Jones |
| 2017/0027978 A1* | 2/2017 | Mukunda ............. A61K 31/352 |

* cited by examiner

*Primary Examiner* — Taofiq A Solola
(74) *Attorney, Agent, or Firm* — patenttm.us

(57) ABSTRACT

A method for extraction of desirable compounds from *cannabis* provides for high-cannabinoid full spectrum (HCFSE) extractions, using $CO_2$ at low temperature to extract the compounds in an extraction vessel. The $CO_2$ with extracted compounds is transferred to a heated vessel which converts the $CO_2$ to a gas, allowing the desired compounds to drop out and be removed.

20 Claims, 1 Drawing Sheet

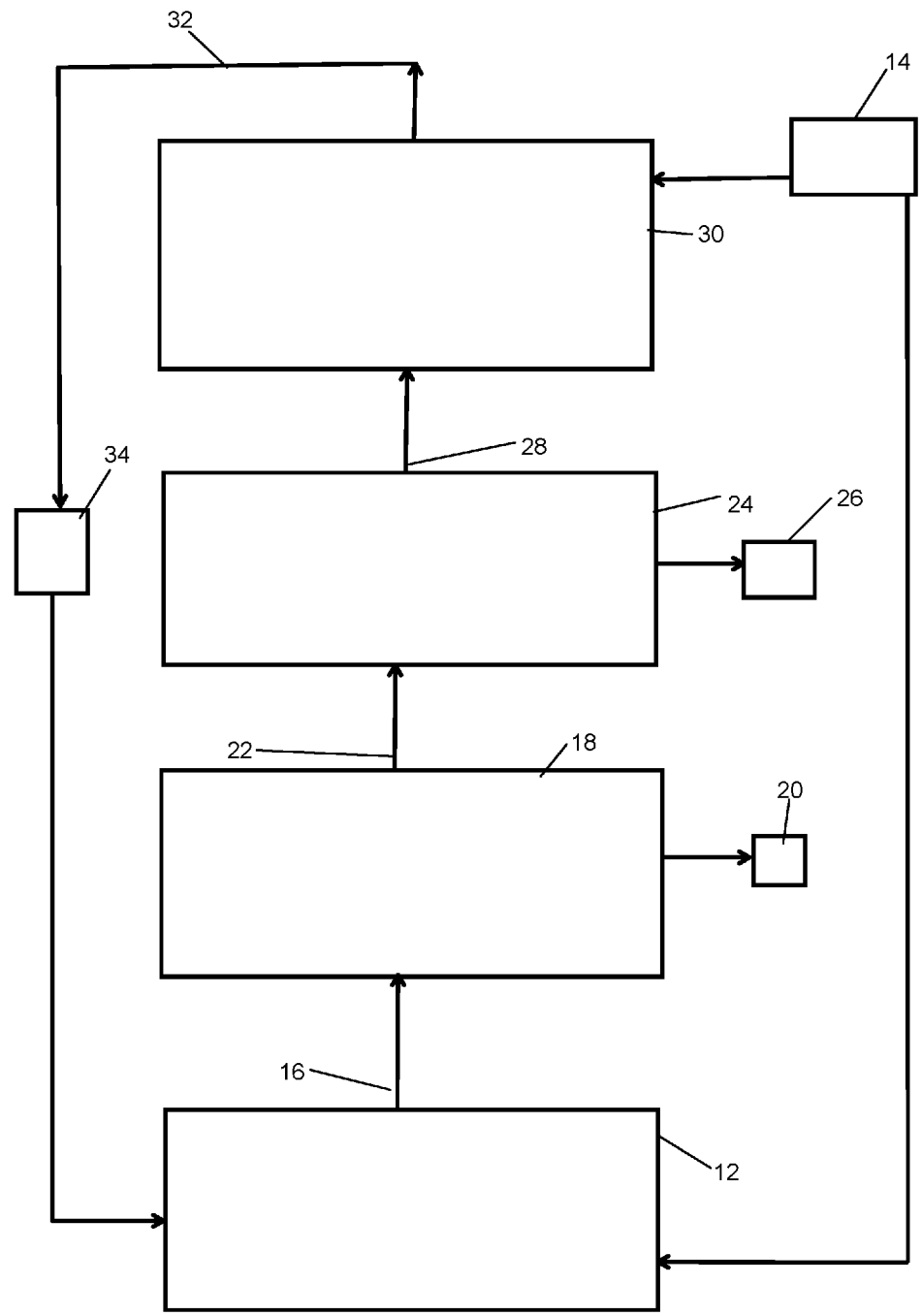

EXTRACTION METHOD

BACKGROUND

This disclosure relates to extraction of substances from botanical specimens, and more particularly to high-cannabinoid full spectrum (HCFSE) extractions from *cannabis*.

In the *cannabis* industry, extracts of *cannabis* plants are desirable to allow uses other than direct use of the plant material. A commonly used method of extraction is hydrocarbon extraction, using propane or butane (or possibly pentane or hexane) to remove cannabinoids and terpenes from the plant material. This method of extraction can be cheaper to operate than other methods, but the process must be done in a carefully prepared environment to avoid explosion and injury.

Other extractors use supercritical $CO_2$ methods, which avoid the danger of explosion, but have much higher equipment costs.

Both hydrocarbon and supercritical and subcritical $CO_2$ extraction result in an output material that can include both desired and undesired compounds from the *cannabis* (such as residual hydrocarbon, wax, etc.), requiring post processing, to remove the hydrocarbons or to remove wax and other components that remain.

SUMMARY

In accordance with the disclosure, a subcritical $CO_2$ process is employed to obtain high-cannabinoid full spectrum (HCFSE) extractions from *cannabis*.

The subject matter of the present technology is particularly pointed out and distinctly claimed in the concluding portion of this specification. However, both the organization and method of operation, together with further advantages and embodiments thereof, may best be understood by reference to the following description taken in connection with accompanying drawings wherein like reference characters refer to like elements.

BRIEF DESCRIPTION OF THE DRAWING

The FIGURE is a block diagram of the extraction system in accordance with the disclosure.

DETAILED DESCRIPTION

The method according to a preferred embodiment of the present disclosure comprises processing an amount of dried *cannabis* in an extraction device using a subcritical $CO_2$ process at pressure and temperature values to extract high-cannabinoid full spectrum (HCFSE) components.

The preferred manner of performing the process, involves, with reference to FIG. 1, a block diagram of the extraction device employed, using an extraction device 10 that comprises an extraction vessel 12. The extraction vessel is jacketed so that the temperature thereof can be controlled and maintained at a desired level. The extraction vessel is connected by pipe 16 to a collection vessel 18. The collection vessel may have a collection valve 20. Vessel 18 is connected by pipe 22 to an optional overflow vessel 24, which may have a collection valve 26. Vessel 24 connects via pipe 28 to gas/liquid phase change jacketed vessel 30, which is connected to extraction vessel 12 via pipe 32, through pump 34. Vessel 30 can receive $CO_2$ from a $CO_2$ supply 14 as desired, which can also supply vessel 12 with $CO_2$. The device thereby provides a looped extraction system.

In use, the specimen which is to have high-cannabinoid full spectrum material extracted therefrom is loaded into extraction vessel 12, the vessel is sealed and the pressure in the vessel is raised to between 500 to 5000 psi by the introduction of fresh $CO_2$ at a temperature of between −60 to +80 degrees F. In a particular example, the specimen will be a quantity of dried or wet (not dried) *cannabis* such that desirable high-cannabinoid full spectrum (HCFSE) components can be extracted therefrom.

The $CO_2$, which will suitably be in a liquid state in vessel 12 will cause the high-cannabinoid full spectrum (HCFSE) components and other compounds to be extracted from the *cannabis*, and operation of pump 34 will move the HCFSE containing $CO_2$ from vessel 12 into vessel 18. Vessel 18 is suitably maintained at 500 psi at a temperature of 130 degrees F. in a particular embodiment. Other embodiments can vary the temperature between 60 to 600 degrees F. Vessel 24 is maintained at 120 to 130 degrees F. and 500 psi, and the high temperature of vessel 18 (and vessel 24) relative to the extraction vessel will cause the $CO_2$ to become a gas, allowing the extracted high-cannabinoid full spectrum components to drop out of the $CO_2$, this dropping out occurring mainly in the extraction vessel 18. The gaseous $CO_2$ with most of the high-cannabinoid full spectrum components removed is then pumped from vessel 18 to vessel 24, vessel 24 operating as an overflow to allow removal of any residual high-cannabinoid full spectrum components remaining with the $CO_2$ gas, to minimize gumming up the rest of the device. Operation of pump 34 then moves the gaseous $CO_2$ from vessel 24 into phase change jacketed vessel 30, which is suitably maintained to 1000 psi (although the pressure can be fluctuated between 300 to 5000 psi) at 40 degrees F. This temperature and pressure returns the $CO_2$ to a liquid state, and the now liquid $CO_2$ is pumped (via operation of pump 34) back into the extraction vessel 12, completing the extraction loop. Each cycle during of operation of the pump moves the $CO_2$ and extracts through the system.

The device is operated for a period of time, such as 2 to 3 hours or as much as 24 hours or more, to allow extraction of a sufficient amount of the desired high-cannabinoid full spectrum (HCFSE) components.

Valve 20 may be opened a slight amount during operation of the device so that the extracted high-cannabinoid full spectrum (HCFSE) components may be continuously collected outside of the device, or may be occasionally opened to allow a quantity of extracted high-cannabinoid full spectrum (HCFSE) components built up in vessel 18 to be removed. Any overflow collected in vessel 24 may be removed via valve 26.

Operation of the device for 2 to 3 hours results in output that is substantially higher in terpenes. Operation for 24 hours results in higher cannabinoid content in the output.

The operational parameters of the device (temperatures and pressures of the various vessels) can be adjusted such that the viscosity of the extracted high-cannabinoid full spectrum (HCFSE) components is at a desired level. For example, if the high-cannabinoid full spectrum (HCFSE) components are to be used as liquid for filling e-cigarette cartridges, a certain consistency range may be desirable. Setting operation of the device to produce the desired consistency can thereby remove the need for post processing to dilute or thicken so that the end product flows as desired.

Use of the system and process, thus provides a high-cannabinoid full spectrum (HCFSE) extraction that is ready to use and that does not require post processing. It is noted that lower pressure and colder temperatures results in higher terpene values in the output.

Examples

TABLE 1 provides examples of results from various pressure levels in the different vessels of the device, illustrating variation of the resulting extractions.

| Extraction Vessel 12 (psi) | Separator 18 (psi) | Separator 24 (psi) | Vessel 30 (psi) | Consistency of output from vessels 18 or 24 |
|---|---|---|---|---|
| 500 | 500 | 500 | 400 | Thin oil No wax HTLC |
| 700 | 500 | 500 | 600 | Thin oil No wax HTLC |
| 900 | 600 | 600 | 700 | Thin oil No wax HTHC |
| 1050 | 600 | 600 | 800 | Thin oil No wax HTHC |
| 1400 | 650 | 650 | 900 | Little thicker No wax HTHC |
| 1700 | 700 | 700 | 1000 | Little thicker Little wax HTHC |
| 2000 | 900 | 900 | 1200 | Little thicker Little wax HTHC |
| What if scenario continue pattern | → | → | → | → |
| 2500 | 1200 | 1200 | 1400 | Thicker More wax HTHC |
| 3000 | 1500 | 1500 | 2000 | Thicker More wax HTHC |
| 4000 | 2000 | 2000 | 3000 | Very thick Heavy wax HTHC |
| 5000 | 2000 | 2000 | 4000 | Very thick Heavy wax HTHC |

HTLC = High Terpene Low Cannabinoid
HTHC = High Terpene High Cannabinoid

From the table it can be seen that operation in the lower ranges of pressures results in an output oil that is thinner, with high terpene content and low cannabinoid content with no wax present. Somewhat higher pressures increase the cannabinoid extraction so that both high terpene and cannabinoid levels are present. As the pressures increase, the resulting output is somewhat thicker, but still without wax. Further pressure increases start to increase the amount of wax present, and still higher pressures result in a thicker output. Extractions have been run with extraction vessel 12 up to 2000 psi, but the results can be predicted that as the pressures are increased, as illustrated in the lower portions of the table, the thickness of the output will increase and the amount of wax extracted will increase.

Variations on the temperatures and pressures (as noted above in table 1) can be made. For example, vessel 12 is typically held to between −60 to +80 degrees F. Vessels 18 and 24 can be operated at between 84 to 200 degrees F.

Typical operational ranges that have been employed are:
Vessel 12: −60 to 80 degrees F., 500 to 2000 psi. Keeping this vessel cold allows extraction to occur without requiring the post processing of the prior art. −10 to −60 is the range most often used.

Vessel 18 −130 degrees F., 500 psi. The warmer temperature of this vessel causes the $CO_2$ to return to a gas state, dropping out the extracted terpenes, cannabinoids and THC Vessel 24 −120-130 degrees F., 500 psi. The bulk of the extraction takes place in vessel 18, this vessel acts as 'overflow' to extract most of the remaining elements not gathered in vessel 18

Vessel 30 −40 degrees F., ~1000 psi

Vessels 18 and 24 will typically have the same parameters.

Thus the device can be operated to provide a high terpene output with low cannabinoid, or a high terpene high cannabinoid output, as desired, with no or little wax content. High terpene can mean between 5 to 100% terpene content in the output, with the terpene content varying on a single extraction run depending on the time, temperature and pressure values employed.

While a preferred embodiment of the technology has been shown and described, it will be apparent to those skilled in the art that many changes and modifications may be made without departing from the broader aspects. The appended claims are therefore intended to cover all such changes and modifications as fall within the true spirit and scope of the technology.

What is claimed is:

1. A method of extracting terpenes, cannabinoids and THC from *cannabis*, comprising the steps of:
    a) placing dried *cannabis* in an extraction vessel;
    b) introducing $CO_2$ into the extraction vessel at an extraction pressure of between 500 to 2000 psi and at temperatures between −50 to 80 F,
    c) thereby extracting components from the *cannabis;*
    d) moving the $CO_2$ with extracted components from the extraction vessel to a first separator held at a first separator pressure of between 500 and 900 psi and a temperature of 60 to 600 degrees F. thereby dropping out extracted terpenes, cannabinoids or THC; and
    e) removing the extracted terpenes, cannabinoids or THC from the first separator.

2. The method according to claim 1, further comprises the steps of moving the $CO_2$ with any remaining extracted components from the first separator to a second separator held at a pressure of between 500 and 900 psi and a temperature of 120 to 130 F; and
    removing any additional extracted terpenes, cannabinoids or THC from the second separator.

3. The method according to claim 1, wherein the extraction pressure is between 500 to 700 psi to extract high terpene low cannabinoid components.

4. The method according to claim 1, wherein the first separator pressure is between 500 to 600 psi to extract high terpene low cannabinoid components.

5. The method according to claim 1, wherein the extraction pressure is between 500 to 700 psi and the first separator pressure is between 500 to 600 psi to extract high terpene low cannabinoid components.

6. The method according to claim 1, wherein the extraction pressure is between 900 to 2000 psi to extract high terpene high cannabinoid components.

7. The method according to claim 1, wherein the first separator pressure is between 600 to 900 psi to extract high terpene high cannabinoid components.

8. The method according to claim 1, wherein the extraction pressure is between 900 to 2000 psi and the first separator pressure is between 600 to 900 psi to extract high terpene high cannabinoid components.

9. The method according to claim 2, wherein the extraction pressure is between 500 to 700 psi to extract high terpene low cannabinoid components.

10. The method according to claim 2, wherein the first separator pressure is between 500 to 600 psi and the second separator pressure is 500 psi to extract high terpene low cannabinoid components.

11. The method according to claim 2, wherein the extraction pressure is between 500 to 700 psi and the first separator pressure is between 500 to 600 psi and the second separator pressure is 500 psi to extract high terpene low cannabinoid components.

12. The method according to claim 2, wherein the extraction pressure is between 900 to 2000 psi and the second separator pressure is between 600 to 1200 psi to extract high terpene high cannabinoid components.

13. The method according to claim 2, wherein the first separator pressure is between 600 to 900 psi and the second separator pressure is between 600 to 1200 psi to extract high terpene high cannabinoid components.

14. The method according to claim 2, wherein the extraction pressure is between 900 to 2000 psi and the first separator pressure is between 600 to 900 psi and the second separator pressure is between 600 to 1200 psi to extract high terpene high cannabinoid components.

15. The method according to claim 1, further comprising
f) cooling the $CO_2$ after the second separator to return it to a liquid state.

16. The method according to claim 15, comprising
g) reintroducing the cooled $CO_2$ to the extraction vessel at an extraction pressure of between 500 to 2000 psi and at temperatures between −50 to 80 F, and
cycling through the steps c through g for a period of 1 to 24 hours.

17. The method according to claim 1, wherein the first separator is held at a temperature of 120 to 130 degrees F.

18. A method of extracting terpenes, cannabinoids and THC from *cannabis*, comprising the steps of:
a) placing *cannabis* in an extraction vessel;
b) introducing $CO_2$ into the extraction vessel at an extraction pressure of between 500 to 2000 psi and at temperatures between −60 to +80 F,
c) thereby extracting components from the *cannabis*;
d) moving the $CO_2$ with extracted components from the extraction vessel to a first separator thereby dropping out extracted terpenes, cannabinoids or THC;
e) cooling the $CO_2$ after the first separator to return it to a liquid state;
f) reintroducing the cooled $CO_2$ to the extraction vessel;
repeating steps c-f for a period of time; and
removing dropped out terpenes, cannabinoids or THC from the first separator.

19. The method according to claim 18, wherein said repeating steps c-f is continued for a period of 1 to 2 hours.

20. The method according to claim 18, wherein said repeating steps c-f is continued for a period of 1 to 24 hours.

* * * * *